United States Patent [19]
Roberts

[11] Patent Number: 5,546,607
[45] Date of Patent: Aug. 20, 1996

[54] HYGIENIC PANTY

[76] Inventor: Mary K. Roberts, 1009 Dunlap La., Knoxville, Tenn. 37914

[21] Appl. No.: 205,831

[22] Filed: Mar. 4, 1994

[51] Int. Cl.$^6$ .................................................. A61F 13/15
[52] U.S. Cl. .................. 2/406; 2/400; 2/401; 604/385.1; 604/385.2
[58] Field of Search .................................. 2/67, 73, 400, 2/401, 402, 403, 404, 405, 406, 407, 408, 409, 79, 227; 450/102, 103, 104, 105, 94; 604/394, 395, 396, 385.2, 385.1

[56] References Cited

U.S. PATENT DOCUMENTS

| | | | |
|---|---|---|---|
| 1,494,044 | 5/1924 | Ward et al. | 2/406 |
| 2,342,187 | 2/1944 | Gardener | 2/400 |
| 3,368,563 | 2/1968 | Scheier | 604/396 |
| 3,718,902 | 1/1988 | Bonito | 604/396 |
| 4,743,239 | 5/1988 | Cole | 604/385 X |
| 4,756,709 | 7/1988 | Stevens | 604/396 X |
| 4,772,281 | 9/1988 | Armstead | 604/358 |
| 4,880,423 | 11/1989 | Green | 604/391 |
| 4,909,804 | 3/1990 | Douglas, Sr. | 604/396 X |
| 4,972,525 | 11/1990 | Hwang | 2/406 |
| 5,098,419 | 3/1992 | Gold | 604/396 |

*Primary Examiner*—Jeanette E. Chapman
*Attorney, Agent, or Firm*—Judy Winegar Goans

[57] ABSTRACT

A hygienic panty is comprised of a front portion, a back portion, and a crotch portion, and if desired, side portions, conventionally joined to form a waist opening and two leg openings, the crotch portion comprising an outer layer made from a waterproof material and an inner layer of any suitable material, and the front portion and back portion comprising an outer layer made from a waterproof material, an inner layer, and at least one absorbent interliner sandwiched between the inner layer and outer layer.

15 Claims, 4 Drawing Sheets

HYGIENIC PANTY

BACKGROUND OF THE INVENTION

This invention relates to clothing and more particularly clothing suitable for use by women who desire to protect against staining or leakage from the flow of bodily fluids.

It is desirable to protect clothing and bedding against staining or leakage from a variety of sources that principally affect women. These sources include, for example, a bloody vaginal discharge that occurs with menstrual flow or following childbirth, abortion, or dilation and curettage of the uterus. Other vaginal discharges may occur as a result of disease. Staining may also occur as a result of medical treatment, where medicines are applied in the perineal area. Finally, incontinence is a relatively common problem among women of childbearing age and above. Staining of underwear is an irritating and sometimes costly problem experienced by many women, while the staining of outerwear or other items is an event that most women find profoundly embarrassing.

DESCRIPTION OF RELATED ART

A variety of products are available to protect against various types of discharge or leakage. The most traditional include sanitary napkins and diapers.

Sanitary napkins tend to be bulky and uncomfortable and prone to leakage. Further, the variety of conditions under which such items may be worn (generally referred to as "heavy flow" and "light flow") means that no single product is likely to meet all needs. Wider, thicker items are associated with greater protection, and there is, in general, a tradeoff between size and comfort. Slimmer, thinner products have been developed to improve comfort, for example, but these may not be suitable for heavy flow. Even "super-absorbency" products are subject to leakage around the edges, leading to the development of products with "wings" along the sides. Leakage due to shifting of the sanitary napkin has been addressed by supplying adhesive tabs by which the pad can be attached to undergarments, but this does not prevent leakage when the undergarment itself shifts with the position of the wearer.

Except for the vaginal sponge, which is worn internally, most sanitary products are disposable and not washable or reusable. These products are utilitarian items typically worn with conventional panties and secured by belts, tabs, and the like, requiring manipulation to secure the sanitary product and to remove soiled items. For example, U.S. Pat. No. 3,489,149 to Larson provides a "menstrual panty" with a pocket into which a sanitary napkin may be inserted. The need for such manipulations of sanitary items is unsatisfactory and calls to mind the necessity for wearing such utilitarian and unattractive items. In cases where the manipulations may not be conducted by the wearer of the item, as in the case of a bedridden or impaired individual, the manipulations are even more undesirable, as they subject the person changing the sanitary product to contact with bodily fluids and thereby to the possibility of exposure to disease.

In the case of minor incontinence, ordinary sanitary products, such as sanitary napkins or the thinner "mini-pads", may be used. The principal product for such cases, however, is the adult, disposable diaper. Like sanitary napkins, diapers are also unesthetic and call to mind the reason for their use. Further, bulky items are generally uncomfortable to wear.

Another approach to this problem involves the use of absorbent panties, such as training pants for infants. One such absorbent panty is described in U.S. Pat. No. 3,720,212 to Kaupin. This patent describes a conventional panty construction with an absorbent layer and a hydrophobic layer both sandwiched between inner and outer layers of knit fabric. Although the Kaupin construction has numerous advantages over the diaper and sanitary napkin, the likelihood of staining the knit fabric would make it less than satisfactory for use during menstrual flow. Further, the design described would be appropriately esthetic for use by children but would continue to call to mind the "training pant" aspect of the product when used by adult or adolescent women.

SUMMARY

The present invention attempts to overcome some of the limitations of the prior art by providing a hygienic panty that is comfortable, attractive and appropriate for use by adult and adolescent women and is similar in general appearance and feel to conventional panties. One object of the invention is to provide a panty that is suitable for daytime or nighttime use to prevent staining and leakage of bodily fluids onto clothing or other objects. Another object of the invention is to provide a garment that can be worn to absorb menstrual flow without the necessity of undue manipulation of sanitary items. A further object of the invention is to provide a garment that is washable and reusable under ordinary conditions without the necessity of direct contact with surfaces contaminated by bodily fluids. These and further objects of the invention will be more fully understood from the following description of the invention.

BRIEF DESCRIPTION OF THE DRAWINGS

In the brief description of the drawings, page 6, lines 3–14.

DESCRIPTION OF THE PREFERRED EMBODIMENT

This invention is a hygienic panty comprising front, back, and crotch portions and, in some embodiments, side portions, all joined conventionally to form a panty. There are six principal embodiments. The various embodiments reflect different arrangements of padding in the front and rear portions and the presence or absence of side portions connecting the front portion and rear portion. The back, front and crotch portions are constructed in layers, preferably with an absorbent interlayer sandwiched between layers in one or more of the back, front, or crotch portions. In the context of this invention, "inner" refers to that layer or surface nearest the skin of the wearer. For each embodiment, the terms "front portion" and "back portion" refer to those portions of the garment extending between side seams, whether those seams connect the front and back portions to each other or to a side portion.

First embodiment

Figure 1:
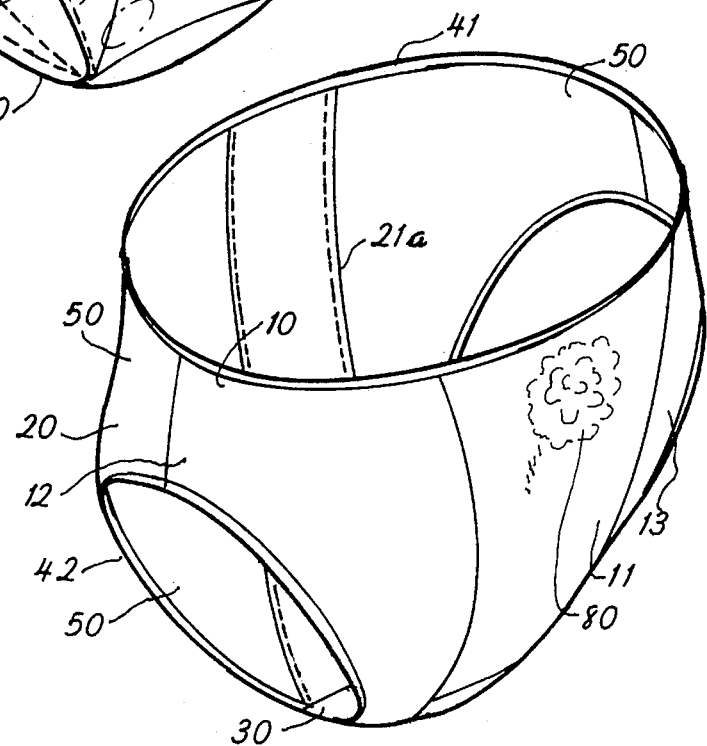
FIG. 1 is an isometric view of a first embodiment of the invention.

Referring now to the drawings, as shown in FIG. 1, the panty has a front portion 10 and back portion 20 joined by a crotch portion 30. The portions 10, 20, and 30 form a waist opening 41 and two leg openings 42, 43.

The crotch portion 30 is formed of an inner layer 50, preferably of a thin cotton knit interlock fabric, and an outer layer 60 of waterproof fabric, such as waterproof nylon. An absorbent interliner 70 may also be sandwiched between inner and outer layers 50 and 60 in the crotch portion 30, but considerations of comfort and bulkiness generally suggest that it is preferable not to include the interliner in the crotch portion 30.

The back portion 20 may be formed of only a single layer 50 preferably of knit fabric. Additional padding may be supplied in across a central portion 21a of the back portion 20 in a narrow strip extending from the edge of the back portion 20 that attaches to the crotch portion 30 to the waist opening 41, as shown in FIGS. 1.

Figure 7:
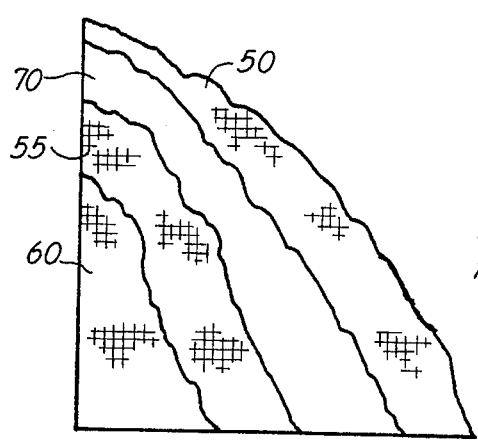
FIG. 7 a cutaway view of the layers of fabric in the padded portion of the invention.

As shown in FIGS. 1, the front portion is constructed in three segments, a central segment 11 and flanking segments 12, 13 on either side of the central segment 11. In this arrangement, the central segment 11 is constructed with an absorbent interliner 70 sandwiched between a knit inner layer 50 and waterproof outer layer 60. The absorbent interliner 70 is placed across the central segment 11. The absorbent interliner 70 is preferably made from a thin layer of non-woven material such as polyester needle-punched fleece or batting, although any flexible, compressible, washable, absorbent material may be substituted. Intermediate the outer layer and absorbent interliner is preferably placed a fourth layer of knit fabric 55, which reduces shifting of the absorbent layer. The preferred arrangement of layers in the padded portion is illustrated in FIG. 7. The flanking segments 12, 13 may preferably be constructed of a single layer only, preferably of knit fabric.

The layers for each portion are seamed together and the portions are then seamed together as shown in the figures. The waist and leg openings 41, 42, 43 are supplied with elastic in a conventional manner. The layers may be anchored at one or more additional points by decorative stitching 80 that extends through the entire thickness of the garment or at least through the outer layers 60, 70.

Second embodiment

Figure 2:
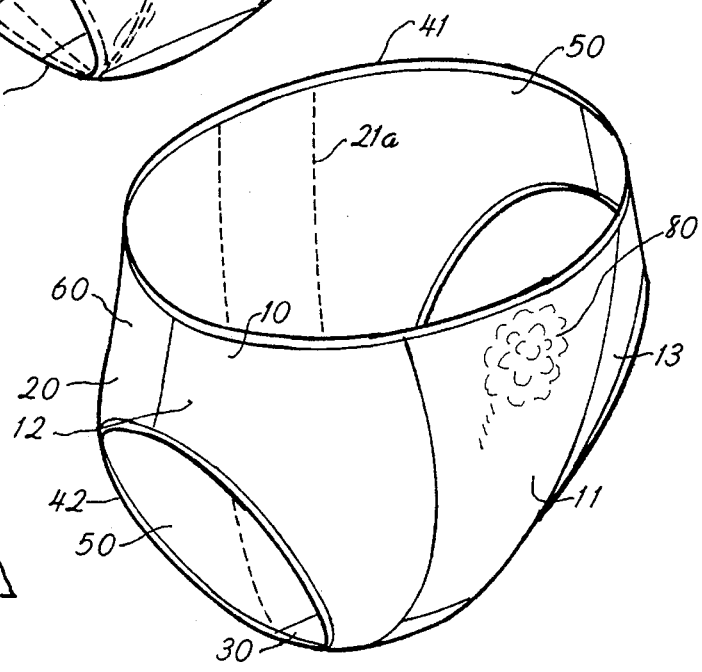
FIG. 2 is an isometric view of a second embodiment of the invention.

A second embodiment is shown in FIG. 2. The front portion 10 and crotch portion 30 in the second embodiment are as described for the first embodiment, and the second embodiment is identical in construction to the first embodiment. The sole difference is that in this embodiment, the back portion 20 is formed of an inner layer 50 preferably of knit fabric and an outer layer 60 of waterproof fabric, such as waterproof nylon. An absorbent interliner 70 may also be sandwiched between inner and outer layers 50 and 60 in the back portion 20, but considerations of comfort and bulkiness generally suggest that it is preferable not to include the interliner in the back portion 20. Preferably, an absorbent interliner 70 is seamed between the inner layer 50 and outer layer 60 across a central portion 21a of the back portion in a narrow strip extending from the edge of the back portion 20 that attaches to the crotch portion 30 to the waist opening 41, as shown in FIG. 2. The preferred arrangement of layers in the padded portion is illustrated in FIG. 7.

Third embodiment

Figure 3:
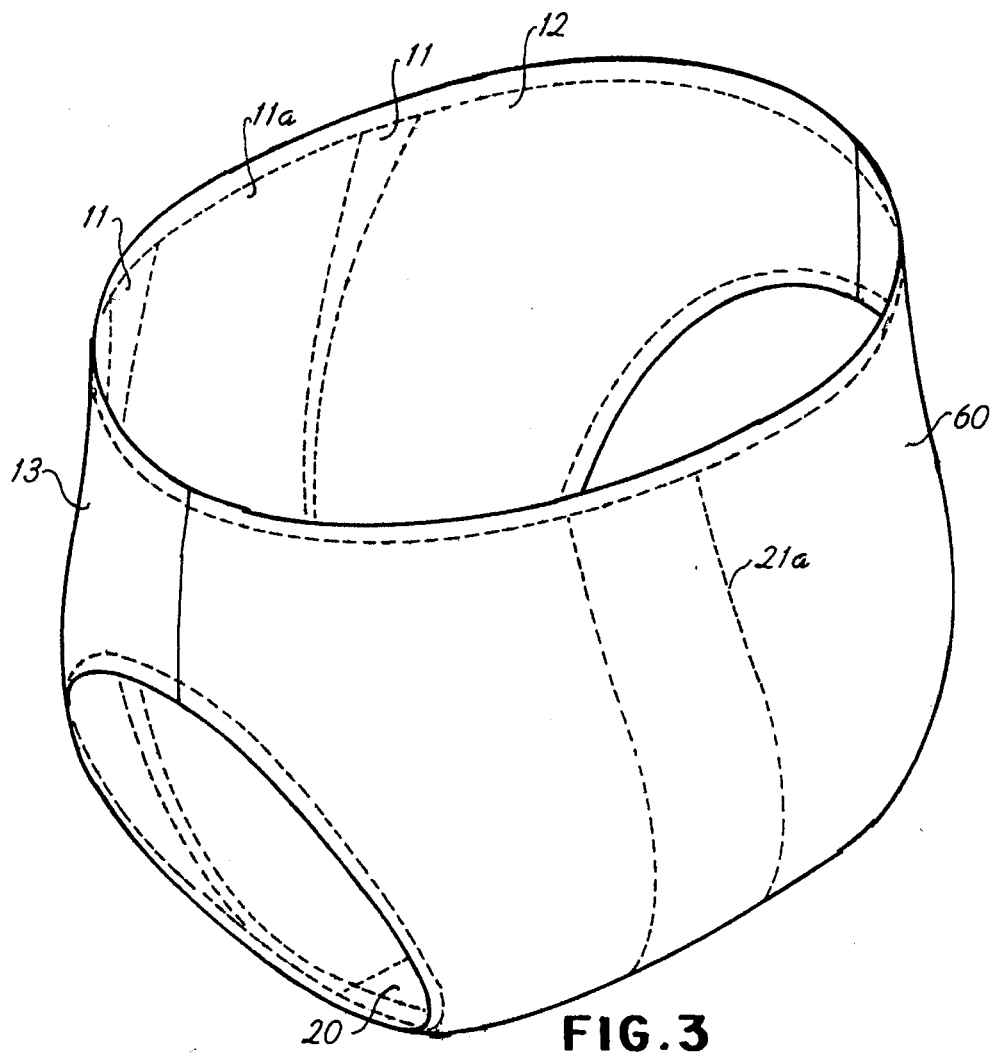
FIG. 3 is a rear isometric view of a third embodiment of the invention.

In a third embodiment, shown in FIG. 3, the back portion 20 and crotch portion 30 and construction are as described for the second embodiment. The sole difference is that padding does not extend across the entire central segment 11 of the front portion 10.

As shown in FIG. 3, the front portion is constructed in three segments, a central segment 11 and flanking segments 12, 13 on either side of the central segment 11. In the third embodiment, the central segment 11 is constructed with an absorbent material sandwiched 70 between a knit inner layer and waterproof outer layer 60.

The absorbent material 60 may be placed across a rectangular strip 11a approximately the width of a conventional sanitary napkin and extending vertically along the center of the front portion 10 in a rectangular shape until it tapers inward at the crotch 30. The layers are seamed together around the perimeter of the central segment 11 or the tapered rectangular segment 11a, thereby anchoring the absorbent material. The layers may be further anchored by decorative stitching (not shown in FIG. 3) that extends through the entire thickness or at least through the two outer layers. In this arrangement, the second interliner intermediate the absorbent and waterproof layers is entirely optional, as the absorbent layer is much less likely to shift or bunch over the smaller area. The flanking segments 12, 13 may preferably be constructed of a single layer only, preferably of knit fabric. The preferred arrangement of layers in the padded portion is illustrated in FIG. 7.

Fourth embodiment

In this embodiment, the panty may have a front portion 15, back portion 25, crotch portion 30, and side portions 45, 46, the front and back portions 15, 25, being joined by the crotch portion 30 and laterally by side portions 45,46. The portions form a waist opening and two leg openings. Since side portions 45, 46 connect front and back portions 15 and 25, for a given size panty, front portion 15 and back portion 25 are somewhat narrower than front portion 10 and back portion 20. The side portions 45, 46 may be formed preferably of a single layer of knit fabric or of a more decorative material, such as lace.

Figure 4:
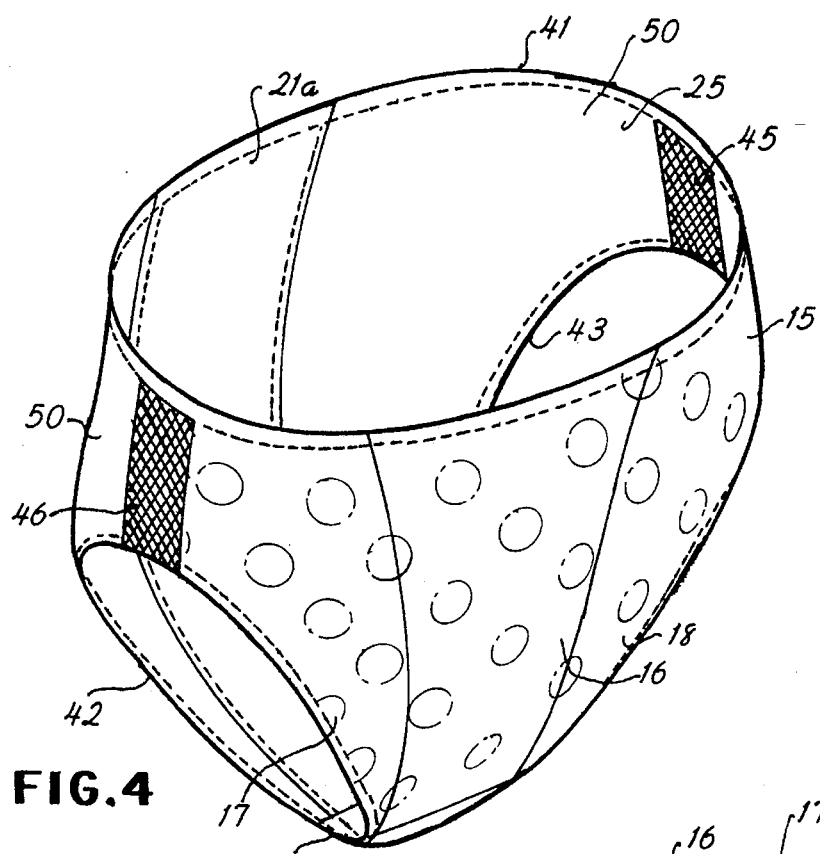
FIG. 4 is an isometric view of a fourth embodiment of the invention.

As shown in FIG. 4, the front portion is constructed in three segments, a central segment 16 and flanking segments 17, 18 on either side of the central segment 16. In this arrangement, the central segment 16 is constructed with an absorbent interliner 70 sandwiched between a knit inner layer 50 and waterproof outer layer 60. The absorbent interliner 70 is placed across the central segment 16. The absorbent interliner 70 is preferably made from a thin layer of non-woven material such as polyester needle-punched fleece or batting, although any flexible, compressible, washable, absorbent material may be substituted. Intermediate the outer layer and absorbent interliner is preferably placed a fourth layer of knit fabric 55, which reduces shifting of the absorbent layer. The preferred arrangement of layers in the padded portion is illustrated in FIG. 7. The flanking segments 17, 18 may preferably be constructed of a single layer only, preferably of knit fabric.

In the fourth embodiment, the back portion 25 is as described for the back portion 20 in the first embodiment, i.e., formed of only a single layer 50 preferably of knit fabric. Additional padding may be supplied in a central portion 21b of the back portion 25 in a narrow strip extending from the edge of the back portion 25 that attaches to the crotch portion 30 to the waist opening 41, as shown in FIG. 4. The crotch portion 30 is identical to that in the first embodiment. The layers may be anchored at one or more additional points by decorative stitching (not shown in FIG. 4) that extends through the entire thickness of the garment or at least through the outer layers 60, 55, 70. As illustrated in FIG. 4, the layers are seamed together around the perimeter of the central segment 16, thereby anchoring the absorbent material.

Fifth embodiment

Figure 5:
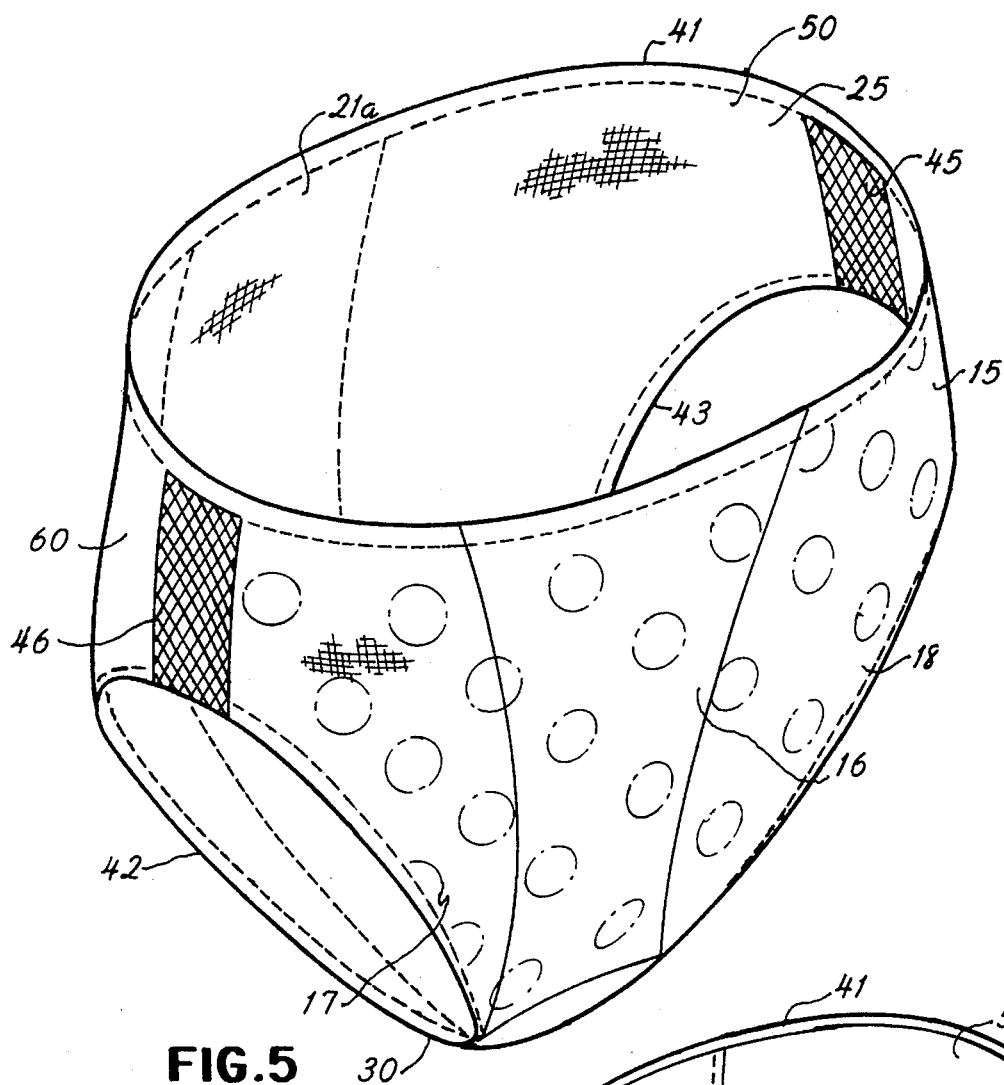
FIG. 5 is an isometric view of a fifth embodiment of the invention.

In this embodiment, the panty has the same portions and construction as in the fourth embodiment. The sole difference is that in this embodiment, the back portion 20 is formed of an inner layer 50 preferably of knit fabric and an outer layer 60 of waterproof fabric, such as waterproof nylon. An absorbent interliner 70 may also be sandwiched between inner and outer layers 50 and 60 in the back portion 20, but considerations of comfort and bulkiness generally suggest that it is preferable not to include the interliner in the back portion 20. Preferably, an absorbent interliner 70 is seamed between the inner layer 50 and outer layer 60 across a central portion 21a of the back portion 20 in a narrow strip extending from the edge of the back portion 20 that attaches to the crotch portion 30 to the waist opening 41, as shown in FIGS. 5.

Sixth embodiment

In the sixth embodiment, the panty has the same portions and construction as in the fourth embodiment. The sole difference is that padding does not extend across the entire central segment 16 of the front portion 15 but is limited to a tapered rectangular strip 16a, as described below.

Figure 6:
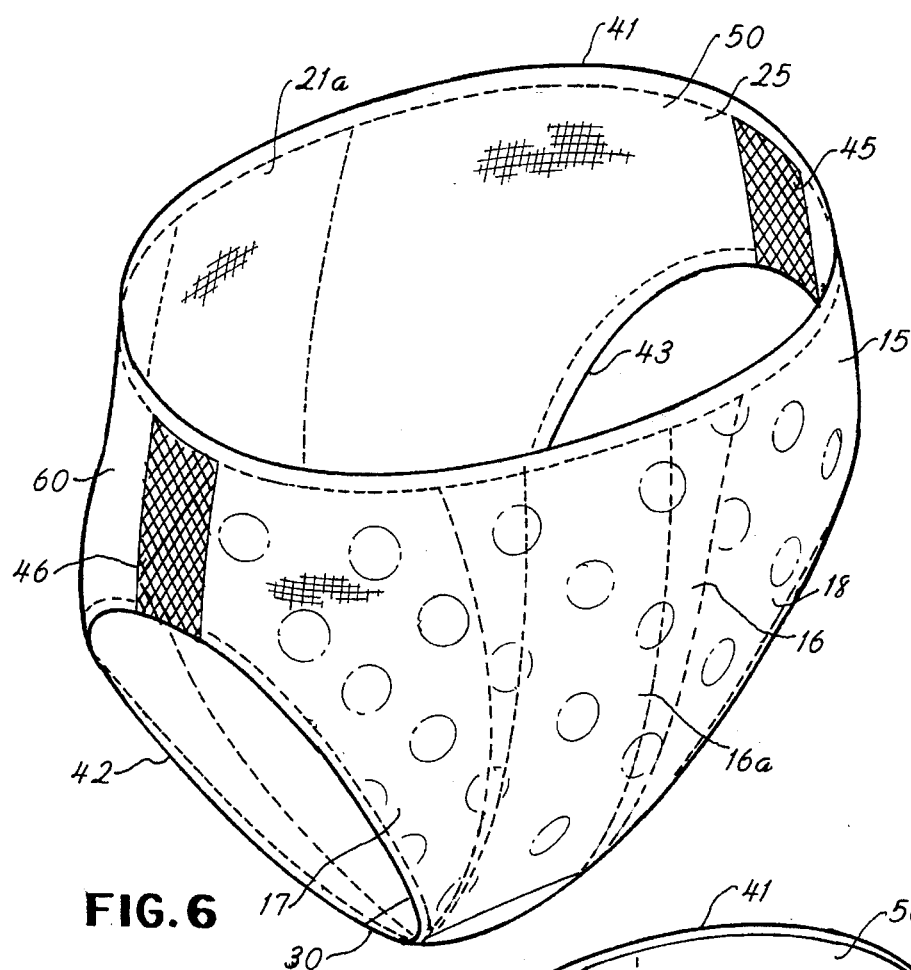
FIG. 6 is an isometric view of a sixth embodiment of the invention.
Figure 8:
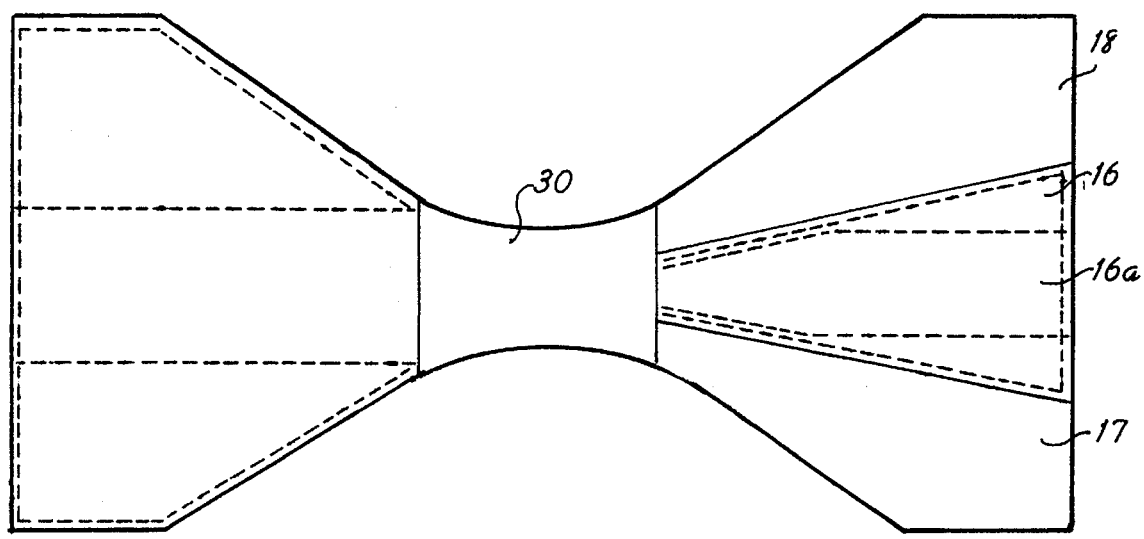
FIG. 8 is a plan view of the partially constructed sixth embodiment of the invention.
Figure 9:
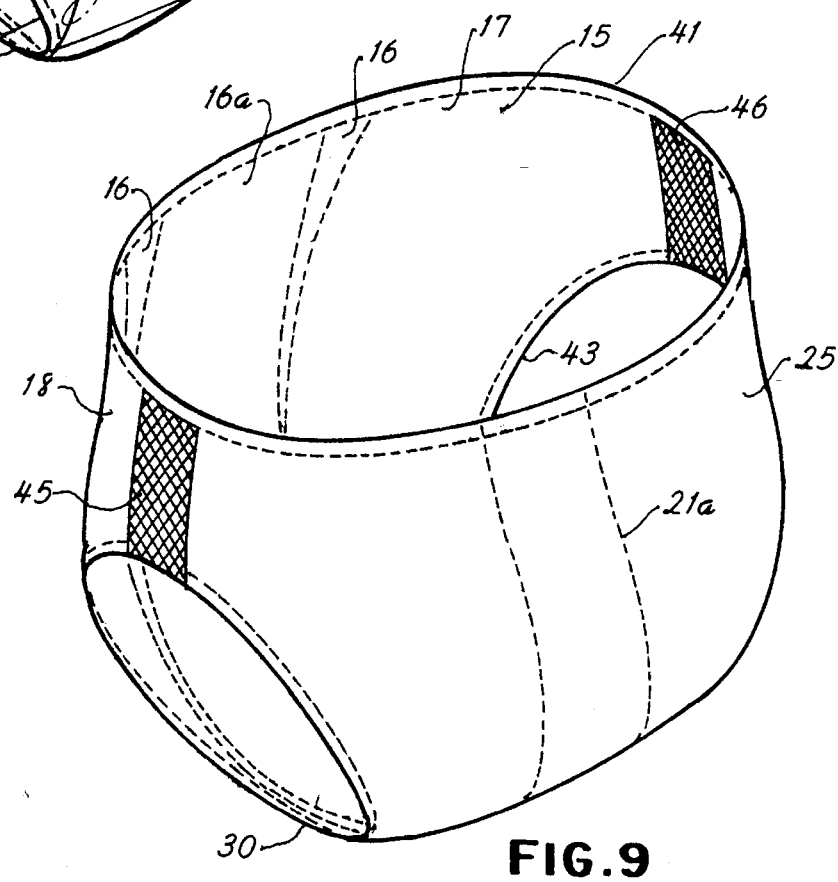
FIG. 9 is a rear isometric view of a sixth embodiment of the invention.

As shown in FIGS. 6, 8, and 9, the front portion is constructed in three segments, a central segment 16 and flanking segments 17, 18 on either side of the central segment 16. In the sixth embodiment, the central segment 16 is constructed with an absorbent material sandwiched 70 between a knit inner layer and waterproof outer layer 60.

The absorbent material 60 may be placed across a rectangular strip 16a approximately the width of a conventional sanitary napkin and extending vertically along the center of the front portion 15 in a rectangular shape until it tapers inward at the crotch 30. This arrangement is illustrated in FIG. 4 for the sixth embodiment. As illustrated in FIG. 4, the layers are seamed together around the perimeter of the central segment 16 or the tapered rectangular segment 16a, thereby anchoring the absorbent material. The layers may be further anchored by decorative stitching (not shown in FIG. 6) that extends through the entire thickness or at least through the outermost layers 60, 70 and if used, the knit layer 55. In this arrangement, the second interliner intermediate the absorbent and waterproof layers is entirely optional, as the absorbent layer is much less likely to shift or bunch over the smaller area. The flanking segments 17, 18 may preferably be constructed of a single layer only, preferably of knit fabric. The back portion 25, crotch portion 30, and construction are as described for the fifth embodiment.

The front portion 15 and the back portion 25 are seamed to the single thickness side portions 45, 46 as shown in FIG. 6. The waist and leg openings are supplied with elastic in a conventional manner.

I claim:

1. A hygienic panty comprising a front portion, a back portion, a crotch portion, and a first and second side portions, said front portion, back portion, first and second side portions, and crotch portion being joined to form a waist opening and two leg openings, said crotch portion comprising an outer layer made from a waterproof material and an inner layer, said front portion comprising a central segment and a first and second flanking segment, said central segment extending from said crotch portion to said waist opening and tapering outward such that the central segment is wider at the waist opening than at the crotch opening, said central segment comprising an outer layer made from a waterproof material, an inner layer, and at least one interliner sandwiched between said inner layer and said outer layer, said interliner extending from the waist opening to the crotch portion, said interliner being essentially rectangular in shape throughout most of its length and tapering inwardly toward the crotch portion, and said first and second flanking segments comprised of a single layer only.

2. The hygienic panty described in claim 1 wherein said interliners include a layer of an absorbent material.

3. The hygienic panty described in claim 2 wherein said absorbent material is needlepunched fleece, said outer layer is waterproof nylon, and said inner layer is knit interlock fabric.

4. The hygienic panty described in claim 3 wherein said interliners further include a layer of knit interlock sandwiched between said needlepunched fleece and said outer layer.

5. The hygienic panty described in claim 3 wherein said first and second side portions are made of lace.

6. The hygienic panty described in claim 1 wherein said back portion includes at least one absorbent interliner sandwiched between said inner layer and said outer layer.

7. A hygienic panty comprising a front portion, a back portion, and a crotch portion, said front portion, back portion, and crotch portion being joined to form a waist opening and two leg openings, said crotch portion comprising an outer layer made from a waterproof material and an inner layer, said front portion comprising a central segment and a first and second flanking segment, said central segment extending from said crotch portion to said waist opening and tapering outward such that the central segment is wider at the waist opening than at the crotch opening, said central segment comprising an outer layer made from a waterproof material, an inner layer, and at least one interliner sandwiched between said inner layer and said outer layer, said interliner extending from the waist opening to the crotch portion, being essentially rectangular in shape throughout most of its length and tapering inwardly toward the crotch portion, and said first and second flanking segments comprised of a single layer only.

8. The hygienic panty described in claim 7 wherein said interliner is needlepunched fleece, said outer layer is waterproof nylon, and said inner layer is knit interlock fabric.

9. The hygienic panty described in claim 7 wherein said back portion includes an interliner of needlepunched fleece.

10. The hygienic panty described in claim 1 wherein said back portion comprises a single layer only.

11. The hygienic panty described in claim 1 wherein said back portion comprises a single knit inner layer and an outer layer of waterproof nylon.

12. The hygienic panty described in claim 1 wherein said back portion further comprises a rectangular padded portion extending from the crotch portion to the waist opening, said padded portion being comprises of an inner layer of knit interlock fabric, a layer of waterproof nylon, and an interliner of needlepunched fleece.

13. The hygienic panty described in claim 7 wherein said back portion comprises a single layer only.

14. The hygienic panty described in claim 7 wherein said back portion comprises a single knit inner layer and an outer layer of waterproof nylon.

15. The hygienic panty described in claim 7 wherein said back portion further comprises a rectangular padded portion extending from the crotch portion to the waist opening, said padded portion being comprises of an inner layer of knit interlock fabric, a layer of waterproof nylon, and an interliner of needlepunched fleece.

* * * * *